United States Patent

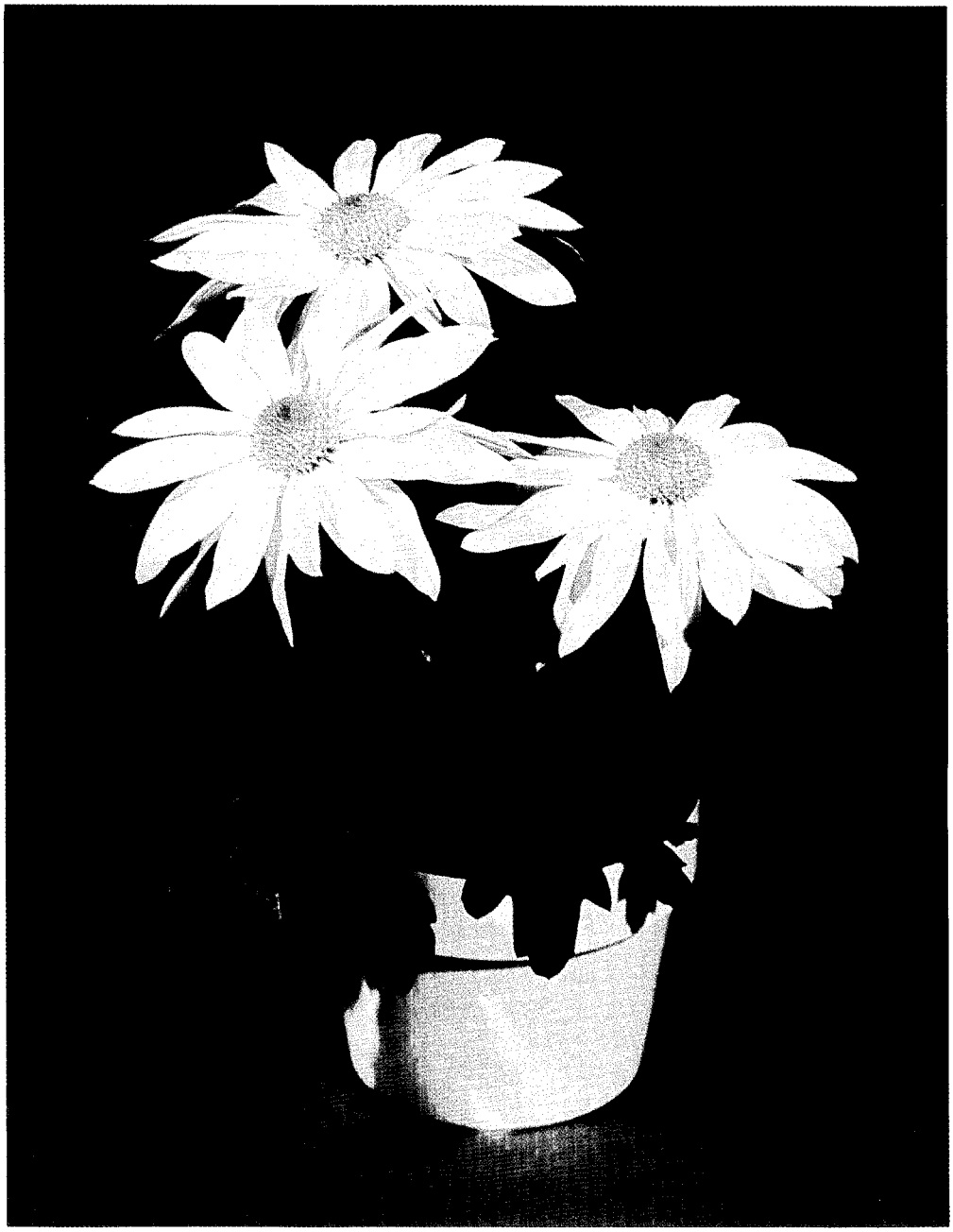

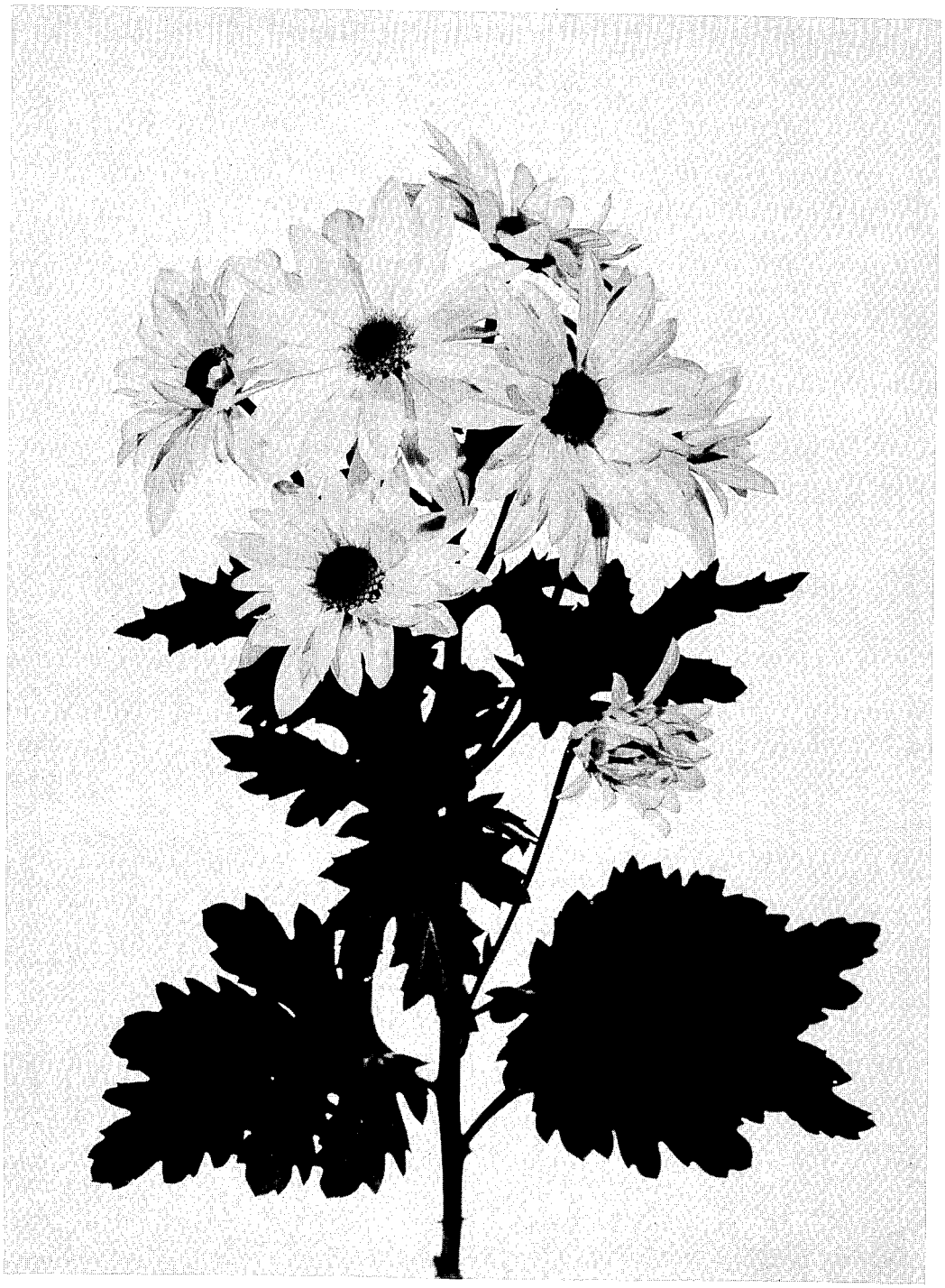

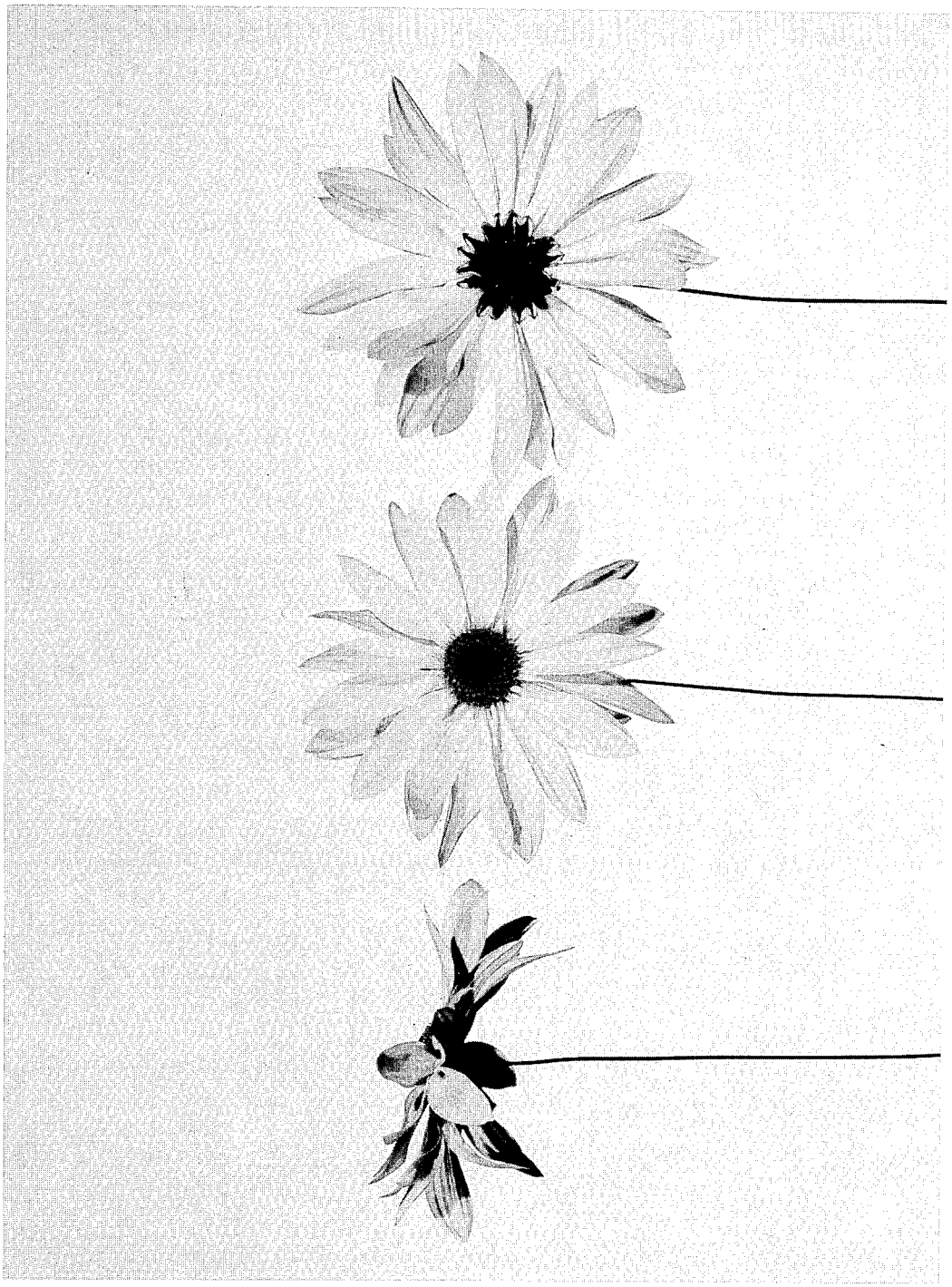

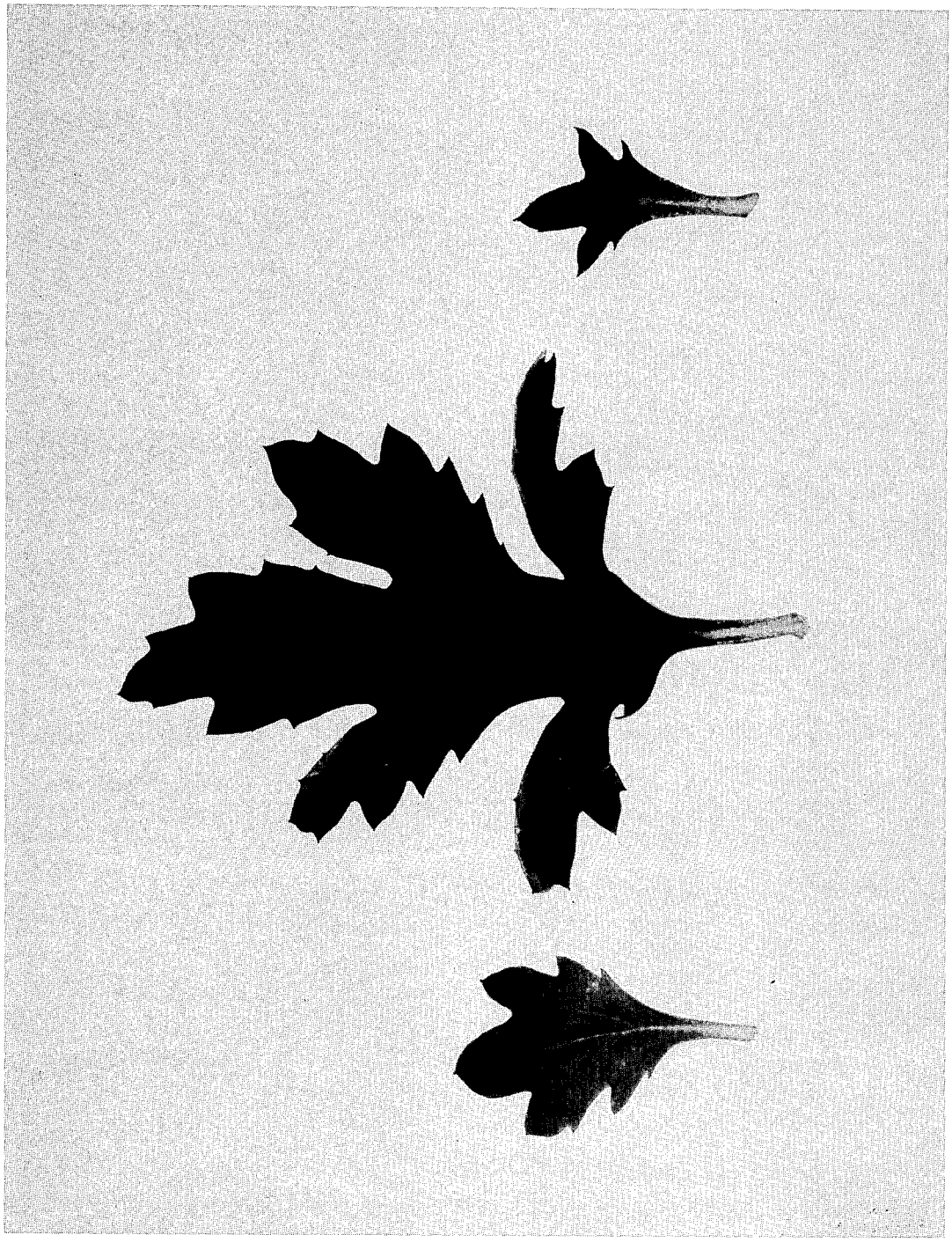

Plant Pat. 3,944
Patented Aug. 24, 1976

3,944

CHRYSANTHEMUM PLANT

Walter H. Jessel, Jr., Doylestown, and William E. Duffett, Akron, Ohio, assignors to Yoder Brothers, Inc., Barberton, Ohio

Filed July 16, 1975, Ser. No. 596,102
Int. Cl.[2] A01H *5/00*
U.S. Cl. Plt.—74 1 Claim

The present invention comprises a new and distinct cultivar of *Chrysanthemum morifolium,* Ramat., hereinafter referred to by the cultivar name Sophisticate (#70009008).

Sophisticate was originated from a cross made in a controlled breeding program in Barberton, Ohio in the year 1969. The female, or seed parent, was 773 (unpatented; commercially available), a white daisy of parentage unknown to the present inventors. The male, or pollen parent, was #67100005 (unnamed seedling), a yellow daisy originated by the present inventors from a cross between Tuneful (#54285007; unpatented; commercially available) and #65741001 (unnamed seedling). Both Tuneful and #65741001 were products of the breeding program of the present inventors.

Sophisticate was discovered and selected as a flowering seedling within the progeny of the slated cross by William E. Duffett and Walter H. Jessel, Jr. on July 8, 1970 in a controlled environment in Barberton, Ohio.

Sophisticate is a product of a planned breeding program which had the objective of creating daisy type cultivars with large inflorescence size and sufficient responsiveness to growth regulators as to be adaptable to cut spray and pot disbud programs. Such traits were not available in combination in previously available cultivars.

The first act of asexual reproduction of Sophisticate was accomplished when vegetative cuttings were taken from the initial selection in September 1970 in a controlled environment in Barberton, Ohio by a technician under formulations established and supervised by William E. Duffett and Walter H. Jessel, Jr. Horticultural examination of selected units initiated Feb. 15, 1971 has demonstrated that the combination of characteristics as herein disclosed for Sophisticate are firmly fixed and are retained through successive generations of asexual reproduction.

The following traits have been repeatedly observed and are determined to be basic characteristics of Sophisticate which in combination distinguish this chrysanthemum as a new and distinct cultivar:

(1) Daisy inflorescence type.

(2) Flat inflorescence form not known to reflex at maturity.

(3) Diameter of face of inflorescence up to 5.5 inches at maturity.

(4) Ivory white ray floret color.

(5) Medium green disc floret color at immature, unopened stage.

(6) Minimal pollen development.

(7) Uniform 9 week (disbud) and 10 week (spray) flowering response period.

(8) Responsiveness to the growth retardant B-9 SP (Alar) for reduction in internode length.

(9) Permanance of inflorescence, averaging from 18–22 days.

The accompanying photographic drawings show typical inflorescence and foliage characteristics of Sophisticate with colors being as nearly true as possible with illustrations of this type. Sheet 1 is a color photograph of Sophisticate grown as a pinched, disbudded plant. Sheet 2 is a black and white photograph of Sophisticate given natural spray treatment with center bud removal. Sheet 3 is a black and white photograph showing three different views of the inflorescence of Sophisticate. Sheet 4 is a black and white photograph showing the foliage of Sophisticate at various stages of growth.

Of the many commercial cultivars known to the present inventors, the most similar existing cultivars in comparison to Sophisticate when grown as a cut spray are White Marble (#54318B08; unpatented) and Bonnie Jean (#21580001; unpatented). Reference is made to Chart C which compares certain characteristics of the above mentioned cultivars with the same characteristics of Sophisticate. General comparisons are as follows:

(1) In comparison to White Marble, Sophisticate has more ivory ray floret color, larger diameter across face of inflorescence, longer flowering response period, shorter plant height and more spreading branching habit. The inflorescence form, inflorescence type, and pollen production of Sophisticate are similar to those of White Marble.

(2) In comparison to Bonnie Jean, Sophisticate has more ivory ray floret color, larger diameter across face of inflorescence, less pollen production, longer flowering response period, taller plant height, and more spreading branching habit. The inflorescence form and inflorescence type of Sophisticate are similar to those of Bonnie Jean.

Of the many commercial cultivars known to the present inventors, the most similar existing cultivars in comparison to Sophisticate when grown as a pinched, disbudded plant is Marguerita 773 (#21680E04; unpatented). Reference is made to Chart D which compares certain characteristics of Marguerita 773 with the same characteristics of Sophisticate.

In comparison in general terms to Marguerita 773, Sophisticate has smaller diameter across face of inflorescence, flatter inflorescence form, and more spreading branching habit. The ray floret color, inflorescence type, pollen production, and flowering response period of Sophisticate are similar to those of Marguerita 773.

In the following description, color references are made to The Munsell Limit Color Cascade, 1972 edition. The color values were determined between 8:00 a.m. and 8:30 a.m. on April 23, 1975 under 160 foot candle light intensity at Barberton, Ohio.

BOTANICAL CLASSIFICATION

*Chrysanthemum morifolium,* Ramat., cv Sophisticate.

I. Inflorescence

A. Capitulum:
- *Form.*—Flat.
- *Type.*—Daisy.
- *Permanence.*—18–22 days.
- *Diameter across face.*—4.0 to 5.5 inches.

B. Corolla of ray florets:
- *Texture (adaxial).*—Glabrous.
- *Appearance and form.*—Ligulate.

*Arrangement.*—Whorled on receptacle.
*Persistence.*—Resists shatter.

*Veination.*—Prominent.
*Margin.*—Deeply serrated.

CHART A—AVERAGE GREENHOUSE CHRYSANTHEMUM ENVIRONMENTS USED FOR BARBERTON, OHIO

| Season | Temperatures used (°F.) Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: on, 5:30 p.m.; off, 7:30 a.m. | From Oct. 15: 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15: 300 p.p.m. |
| Summer | 62 to 68 | 70 to 90 | 65 to 75 | 1 to 2 weeks at 3 hours per night of 7–10 f.c. | On, 6:00 p.m.; off, 8:00 a.m. | None. |

NOTE.—For intensity of direct solar radiation, refer to Chart B.

*Color (abaxial).*—26–3 to white.
*Color (adaxial).*—26–3 to white.

C. Corolla of disc florets: Gamopetalous; tubular; 5-lobed.
*Color.*—23–10 to 27–6.

D. Reproductive organs:
*Androecium.*—Present disc florets only; syngenesious stigma; scant pollen.
*Gynoecium.*—Present both ray and disc florets; inferior, bicarpellate ovary; single style; 2-lobed stigma.

II. Plant

A. General appearance: Semi-spreading; medium height.
B. Duration and texture: Perennial; herbaceous.
C. Foliage:
*Color (abaxial).*—21–14 to 21–16.
*Color (adaxial).*—21–12 to 21–13 overlaid with white
*Shape.*—Spatulate; deeply lobed.
*Texture.*—Glabrous.
*Arrangement.*—Alternate.

CHART B

INTENSITY OF DIRECT SOLAR RADIATION

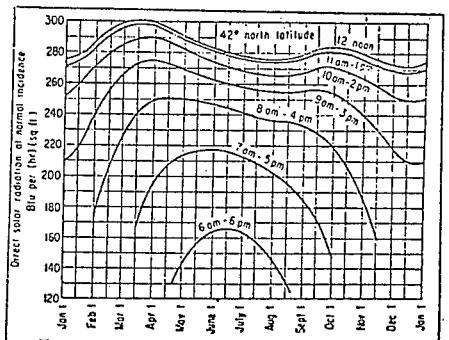

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF SOPHISTICATE, BONNIE JEAN AND WHITE MARBLE

| Cultivar | Ray floret color | Diameter across face of inflorescence (inches) | Inflorescence form and type | Occurrence of pollen | Flowering response period (weeks) | Plant height | Branching habit |
|---|---|---|---|---|---|---|---|
| Sophisticate | Ivory white | 4.0 to 4.5 | Flat daisy | Scant to none | 10 | Medium | Semi-spreading. |
| Bonnie Jean | White | 3.0 to 3.5 | do | Abundant | 9 | Short | Semi-upright. |
| White marble | do | 3.0 to 3.5 | do | Scant | 9 | Tall | Upright. |

NOTE.—Comparisons made of plants grown as cut sprays in a greenhouse in Barberton, Ohio, under conditions as described in Chart A and Chart B.

CHART D—COMPARISON OF SPOHISTICATE AND MARGUERITA 773

| Cultivar | Ray floret color | Diameter across face of inflorescence (inches) | Inflorescence form and type | Occurrence of pollen | Flowering response period (weeks) | Branching habit |
|---|---|---|---|---|---|---|
| Sophisticate | Ivory white | 4.0 to 5.5 | Flat daisy | Scant to none | 9 | Semi-spreading. |
| Marguerita 773 | do | 5.0 to 6.0 | Semi-incurved daisy | do | 9 | Semi-upright. |

NOTE.—Comparisons made of pinched, disbudded plants grown in a greenhouse in Barberton, Ohio, under conditions as described in Chart A and Chart B.

We claim:

1. A new and distinct cultivar of chrysanthemum known by the cultivar name Sophisticate and particularly characterized as to uniqueness by the combined features of daisy inflorescence type; flat inflorescence form not known to reflex at maturity; diameter of face of inflorescence up to 5.5 inches at maturity; ivory white ray floret color; medium green disc floret color at immature, unopened stage; minimal pollen development; uniform 9 week (disbud) and 10 week (spray) flowering response period; responsiveness to the growth retardant B–9 SP (Alar) for reduction in internode length, and permanence of inflorescence averaging from 18–22 days.

No references cited.

ROBERT E. BAGWILL, Primary Examiner